United States Patent [19]

Bolling et al.

[11] Patent Number: 5,124,255
[45] Date of Patent: Jun. 23, 1992

[54] CKS METHOD OF PROTEIN SYNTHESIS

[75] Inventors: Timothy J. Bolling, Gurnee; Wlodzimierz Mandecki, Libertyville, both of Ill.

[73] Assignee: Abbott Laboratories, Abbott Park, Ill.

[21] Appl. No.: 276,263

[22] Filed: Nov. 23, 1988

Related U.S. Application Data

[63] Continuation-in-part of Ser. No. 167,067, Mar. 11, 1988, abandoned.

[51] Int. Cl.[5] .................. C12N 15/00; C12N 15/63; C12N 15/67; C12P 21/06
[52] U.S. Cl. ....................... 435/69.3; 435/69.1; 435/172.3; 435/320.1; 435/69.7; 536/27; 935/22; 935/38; 935/47
[58] Field of Search .............. 435/69.1, 69.3, 69.7, 435/71.2, 172.3, 193, 252.3; 935/27, 29, 41, 47, 48, 72

[56] References Cited

PUBLICATIONS

Szoka, et al., DNA 5(1):11–20 (1986).
Goldman, et al., J. Biol. Chem. 261(34):15831–15835 (1986).
Ray, et al., J. Bacteriology 145(3):1273–1280 (1981).
Glasser, et al., Proc. Natl. Acad. Sci. USA 84:4007–4011 (1987).
Gatenby, et al., Gene 45:11–18 (1986).
Chang et al., Science 228:93–96 (1985).
Gibson, et al., Gene 53:283–286 (1987).

Primary Examiner—Robert A. Wax
Assistant Examiner—Johnny F. Railey, II
Attorney, Agent, or Firm—Daniel W. Collins

[57] ABSTRACT

Disclosed is a method of producing fusion proteins wherein one part of the fusion protein is formed from the bacterial protein CKS.

21 Claims, 18 Drawing Sheets

FIG. 4
SYNTHETIC PROMOTER REGION OF pTB201

```
EcoRI                                                                                    PROMOTER                    TRANSCRIPTION START
 |          -60   Oligo 1                                                     -35                         -10  Oligo 3   1
AATTCCCATTAATTGAGTTAGCTCACTCATTAGGCACCCCAGGCTTTACTTTATGTTCCGGCTCGTATTTGTTGGAATTGTGAGGGATAACAATTGGG
        GGGTAATTAACTCAATCGAGTGAGTAATCCGTGGGGTCCGAAATGAAATACAAGGCCGAGCATAAAACACACTTAACACTCGCCTATTGTTAACCC-
                         Oligo 2                                                   A                           Oligo 4

RBS                                                                       SalI            HpaII
BamHI                                                                                  |              90 |
 |     30 |GATCCAGTAAGGAGGTTTAAATGAGTTTTGTGGTCATTATTCCCGGCGCTACGCGTCGACGCGTCTGCC
         CTAG|GTCATTCCTCCAAATTTACTCAAACACCAGTAATAAGGGGCCGCGATGCGCAGCTGCGCAGACGGC
              METSerPheValValIleIleProAlaArgTyrAlaSerThrArgLeuPro
                                                                kdsB Gene
                                            B
```

| NO. | Y. POS. | AREA | MARK | % |
|---|---|---|---|---|
| 1 | 83.8 | 6.753 | | 0.0 |
| 2 | 85.1 | 235.503 | | 0.3 |
| 3 | 86.5 | 38.445 | | 0.0 |
| 4 | 88.6 | 513.300 | | 0.7 |
| 5 | 90.7 | 673.238 | > | 1.0 |
| 6 | 92.8 | 573.726 | > | 0.8 |
| 7 | 94.2 | 101.197 | > | 0.2 |
| 8 | 95.0 | 319.117 | > | 0.4 |
| 9 | 95.7 | 267.394 | > | 0.4 |
| 10 | 96.8 | 1640.438 | > | 2.5 |
| 11 | 98.2 | 1330.840 | > | 2.0 |
| 12 | 99.1 | 908.457 | > | 1.3 |
| 13 | 100.2 | 1297.070 | > | 1.9 |
| 14 | 101.4 | 353.679 | > | 0.5 |
| 15 | 103.1 | 1716.504 | > | 2.6 |
| 16 | 104.8 | 1644.469 | > | 2.5 |
| 17 | 107.4 | 49672.63 | | 76.4 |
| 18 | 110.8 | 216.800 | > | 0.3 |
| 19 | 111.9 | 53.242 | | 0.0 |
| 20 | 112.7 | 46.527 | | 0.0 |
| 21 | 113.7 | 345.621 | > | 0.5 |
| 22 | 116.0 | 134.054 | > | 0.2 |
| 23 | 116.8 | 9.308 | | 0.0 |
| 24 | 117.4 | 28.648 | | 0.0 |
| 25 | 118.8 | 262.964 | | 0.4 |
| 26 | 120.5 | 663.109 | > | 1.0 |
| 27 | 122.3 | 917.160 | > | 1.4 |
| 28 | 124.7 | 953.421 | > | 1.4 |
| 29 | 126.8 | 7.957 | | 0.0 |
| 30 | 127.8 | 63.953 | | 0.0 |

TOTAL 64995.53

FIGURE 9-1

P120_SYNP41FL    Linear      LENGTH = 1199   (PART 1)

BamHI    (NarI)
      |        |
  1 CTCTGGATCCCCCGGGACCCGGGTGGTGGTGACATGCCTGACAACTGCCGTTCTGAACTGTACAAATAC      69
    LeuTrpIleProGlyAspProGlyGlyGlyAspMETArgAspAsnTrpArgSerGluLeuTyrLysTyr
                                                                     6

INSERT 1

70 AAAGTTGTTAAAATCGAACCGCTGGGTGTTGCTCCGACTAAAGCTAAACGTCGTGTTGTTCAGCGTGAA     138
    LysValValLysIleGluProLeuGlyValAlaProThrLysAlaLysArgArgValValGlnArgGlu

139 AAACGCGCCGTTGGTATCGGTGCACTGTTCCTGGGTTCCTGGTGCTGCTGGTTCTACCATGGGTGCT      207
    LysArgAlaValGlyIleGlyAlaLeuPheLeuGlyPheLeuGlyAlaAlaGlySerThrMETGlyAla

208 GCTTCTATGACCCTGACTGTTCAGGCCCGTCAGCTTCGTCTGTATCGTTCAGCAGCAGAACAATCTG     276
    AlaSerMETThrLeuThrValGlnAlaArgGlnLeuLeuSerGlyIleValGlnGlnGlnAsnAsnLeu

277 CTGGTGTCTATCATCACGTTGAAGCTCAGGAGCATCTGCTGCAACTGACCGTTTGGGGTATCAAACAGCTTCAGGCT  345
    LeuArgAlaIleGluAlaGlnGlnHisLeuLeuGlnLeuThrValTrpGlyIleLysGlnLeuGlnAla

346 CGTATCCTGGCTGTTGAACGTTACCTGAAAGACCAGCAGCTGCTGGGTATCTGGGGTTGCTCTGGTAAA     414
    ArgIleLeuAlaValGluArgTyrLeuLysAspGlnGlnLeuLeuGlyIleTrpGlyCysSerGlyLys

415 CTGATCTGCACTACTGCTGTTCCGTGAACGCTTCTTGGTCTAACAAATCTCTGGAACAGATCTGGAAC     483
    LeuIleCysThrThrAlaValProTrpAsnAlaSerTrpSerAsnLysSerLeuGluGlnIleTrpAsn

FIGURE 9-2 (PART 2)

P120_SYNP41FL  Linear   LENGTH = 1199 (PART 2)

```
484  AACATGACTTGATGGAATGGACCGTGAAATCAACAACTACACAAGCTTGATCCACTCTGATCGAA   552
     AsnMETThrTrpMETGluTrpAspArgGluIleAsnAsnTyrThrSerLeuIleHisSerLeuIleGlu

XbaI
553  GAAAGCCAGAACCAGCAGGAAAAAAACGAACAGGAACTTCTAGAACTGGAACAATGGCTTCTCTGTGG   621
     GluSerGlnAsnGlnGlnGluLysAsnGluGlnGluLeuLeuGluLeuGlnTrpAspLysTrpAlaSerLeuTrp
                                                   592
                              INSERT 2
622  AACTGGTTTAACATCACCAACTGTCTGGTACATCAAACTGTTCATCATGATCGTTGGTGGTCTGGTT   690
     AsnTrpPheAsnIleThrAsnCysLeuValHisLysLeuPheIleMETIleValGlyGlyLeuVal

HpaI
691  GGTCTCGGTATCGTTTTCGCTGTTGTCTGTTCTGTTGTTAACCGTTGTCAGGGTTACTCTCCGCTGTCT   759
     GlyLeuArgIleValPheAlaValLeuSerValValAsnArgValArgGlnGlyTyrSerProLeuSer
                                          727

760  TTCCAGACCCATCTGCCGATCCCGCGTGGTCCGGACCGTCCGGAAGGTATCGAAGAAGAAGGCGGCGAA   828
     PheGlnThrHisLeuProIleProArgGlyProAspArgProGluGlyIleGluGluGluGlyGlyGlu

829  CGTGACCGTGACCGTTCCATCTCTCTGGTAAACGTTCTCTGCTCTGATCGGGACGATCTGCGTTCT   897
     ArgAspArgAspArgSerIleSerLeuValAsnGlySerLeuAlaLeuIleTrpAspAspLeuArgSer
```

FIGURE 9-3

P120_SYNP41FL    Linear    LENGTH = 1199 (PART 3)

898  CTGTGCCTGCTGTTCTCTTACCACCGTCTGCGTGATCGTGCTGCTGATCGTGACTCGTGTATCGTTGAACTGCTC  966
     LeuCysLeuPheSerTyrHisArgLeuArgAspLeuLeuLeuIleValThrArgIleValGluLeuLeu

967  GGCCGTCGTGGTTGGGAAGCTCTGAAATACTGGTGAATCTGTTCAGTACTGGTCCCAGGAACTGAAA  1035
     GlyArgArgGlyTrpGluAlaLeuLysTyrTrpTrpAsnLeuLeuGlnTyrTrpSerGlnGluLeuLys

1036 AACTCTGCTGTTTCTCTGCTGAACGCTACTGCTATCGCTGTTGCTGAAGGCACCGATCGTGTTATCGAA  1104
     AsnSerAlaValSerLeuLeuAsnAlaThrAlaIleAlaValAlaGluGlyThrAspArgValIleGlu

1105 GTAGTTCAGGGTGCTTACCGTGCTATCCGTCACATtCCCGGTCCGTCCGTATCCGTCTGGAACGTATC  1173
     ValValGlnGlyAlaTyrArgAlaIleArgHisIleProArgArgIleArgGlnGlyLeuGluArgIle

KpnI
1174 CTGCTGTAAGCAGGTGGTACCTGCCG  1199
     LeuLeu                1194

SYNTHETIC HIV-2 TMP FRAGMENT SEQUENCE

```
HindIII    BglII                     27                                              54
AGC TTA AAG ATC TAC TCT TCC GCT CAC GGC CGT CAC ACC CGT GGC GTT TTC GTT
Ser Leu Lys Ile Tyr Ser Ser Ala His Gly Arg His Thr Arg Gly Val Phe Val
linker sequences—|—HIV-2 TMP—

81                                             108
CTG GGC TTC CTG GGC TTC CTG GCT ACC GCG GGC TCC GCT ATG GGC GCT GCT TCC
Leu Gly Phe Leu Gly Phe Leu Ala Thr Ala Gly Ser Ala MET Gly Ala Ala Ser 135                                             162
CTG ACC GTT TCC GCT CAG TCC CGT ACC CTG CTG GCT GGC ATC GTT CAG CAG CAG
Leu Thr Val Ser Ala Gln Ser Arg Thr Leu Leu Ala Gly Ile Val Gln Gln Gln 189                                             216
CAG CAA CTT CTA GAC GTT GTT AAA CGT CAG CAG GAG CTC CTG CGT CTG ACC GTT
Gln Gln Leu Leu Asp Val Val Lys Arg Gln Gln Glu Leu Leu Arg Leu Thr Val 243                                             270
TGG GGC ACC AAA AAC CTG CAG GCT CGT GTT ACC GCT ATC GAA AAA TAC CTG CAG
Trp Gly Thr Lys Asn Leu Gln Ala Arg Val Thr Ala Ile Glu Lys Tyr Leu Gln 297                                             324
GAC CAG GCT CGT CTG AAT TCC TGG GGC TGC GCT TTC CGT CAG GTT TGC CAC ACC
Asp Gln Ala Arg Leu Asn Ser Trp Gly Cys Ala Phe Arg Gln Val Cys His Thr

NcoI    SalI
ACC GTT CCA TGG TCG A
Thr Val Pro Trp Ser
                |-linker——
```

CKS METHOD OF PROTEIN SYNTHESIS

This application is a continuation-in-part of application Ser. No. 167,067, filed Mar. 11, 1988, now abandoned.

BACKGROUND OF THE INVENTION

This invention relates to methods for producing proteins in microbial hosts, particularly fusion proteins. The invention also relates to cloning vehicles for transformation of microbial hosts.

It is well established that prokaryotic or enkaryotic proteins can be expressed in microbial hosts where such proteins are not normally present in such hosts (i.e. are "heterologous" to the cells). Generally, such protein expression is accomplished by inserting the DNA sequence which codes for the protein of interest downstream from a control region (e.g. a lac operon) is plasmid DNA, which plasmid is inserted into the cell to "transform" the cell so it can produce (or "express") the protein of interest.

Despite this conceptually straightforward procedure, there are a number of obstacles in getting a cell to synthesize a heterologous protein and subsequently, to detect and recover the protein. The heterologous gene may not be efficiently transcribed into messenger RNA (mRNA). The mRNA may be unstable and degrade prior to translation into the protein. The ribosome binding site (RBS) present on the mRNA may only poorly initiate translation. The heterologous protein produced may be unstable in the cell or it may be toxic to the cell. If no antibodies to the protein are available or if there is no other way to assay for the protein it may be difficult to detect the synthesized protein. Lastly, even if the protein is produced, it may be difficult to purify.

Fusion systems provide a means of solving many of the aforementioned problems. The "carrier" portion of the hybrid gene, typically found on the 5' end of the gene, provides the regulatory regions for transcription and translation as well as providing the genetic code for a peptide which facilitates detection (Shuman et al., J. Biol. Chem. 255, 168 (1980)) and/or purification (Moks et al., Bio/Technology 5, 379 (1987)). Frequently, potential proteolytic cleavage sites are engineered into the fusion protein to allow for the removal of the homologous peptide portion (de Geus et al., Nucleic Acids Res. 15, 3743 (1987); Nambiar et al., Eur. J. Biochem. 163, 67 (1987); Imai et al., J. Biochem. 100, 425 (1986)).

When selecting a carrier gene for a fusion system, in addition to detectability and ease of purification, it would be extremely advantageous to start with a highly expressed gene. Expression is the result of not only efficient transcription and translation but also protein stability and benignity (the protein must not harm or inhibit the cell host).

SUMMARY OF THE INVENTION

This invention is a process for making proteins where a fusion protein of an *E. coli* enzyme, CKS (CTP:CMP-3-deoxy-D-manno-octulosonate cytidylyl transferase or CMP-KDO synthetase), and a heterologous protein is expressed in cells transformed with a cloning vehicle which has a DNA insert coding for CKS and the heterologous protein. The level of expression of CKS fusion protein in cells transformed with such cloning vehicles is quite high, in some instances up to 50 percent of total cellular protein.

BRIEF DESCRIPTION OF THE DRAWINGS

FIG. 4 is the DNA sequence for a synthetic lacP-type promoter used in the cloning vehicles of this invention;

FIG. 9 is a sequence of the synthetic p41 full-length gene with the carboxy terminus of p120. The broken line over the sequence indicates the sequence of pTB310B. The sequence of pTB310A is the same as pTB310B except for the deletion of an A (nt 813) indicated by the Δ. Plasmid pTB321 includes Insert 1 (nt 15-143) which encode the carboxy terminus of p120. Plasmid pTB322 contains Insert 2 (nt 610-720) which encodes the hydrophobic region of p41.

FIG. 14 presents the DNA and amino acid sequences of the synthetic HIV-2 TMP fragment including Hind III/Bgl II linker sequences located 5' and a Sal I linker sequence located 3' to the HIV-2 TMP fragment.

DETAILED DESCRIPTION

1. General

Figure 1:
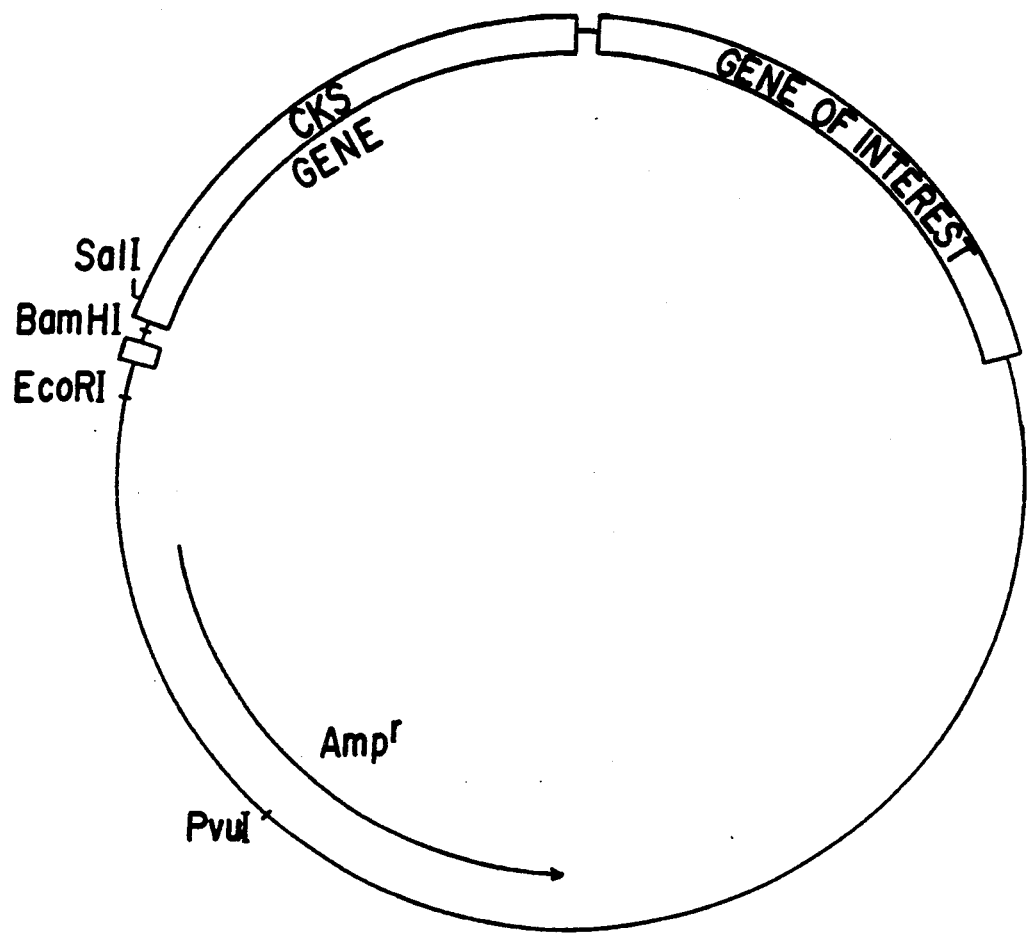
FIG. 1 is a graphic representation of a plasmid cloning vehicle of this invention.

This invention involves the expression of a gene coding for a protein of interest using a DNA cloning vehicle which includes a control region, a region coding for the bacterial enzyme CKS (CMP-KDO synthetase), and a region coding for the protein of interest. The cloning vehicles of this invention are capable of expressing fusion proteins (i.e. CKS—heterologous protein fusions) at high levels. The invention is illustrated in FIG. 1 which shows generically the features of a plasmid of this invention. The plasmid of this invention includes a control region (e.g a lac-type promoter with a sequence for a synthetic ribosome binding site), followed by a gene encoding CKS, which is linked to a gene coding for a heterologous protein of interest.

While fusion proteins per se are well established in the art, the use of CKS as a fusion system is novel. In addition to facilitating detection and purification of heterologous proteins, the expression vector of this invention utilizes the kdsB gene (encoding CKS) which, with the appropriate control region, expresses at higher levels than any other gene in *E. coli* in our hands.

2. Control Region

The control region of this invention is shown in FIG. 4. It includes a modified lac promoter which is essentially native lacP from −73 to +21 with two modifications: 1) a deletion at 23 of one G/C base pair, and 2) a T-A substitution at the −9 position. The control region also includes a synthetic ribosome binding site (nt 31-39) which is homologous to the 3' end of the 16S rRNA (ribosomal ribonucleic acid) in *E. coli*. Following the ribosome binding site is a consensus spacer region which is followed by the ATG translation initiation codon, followed by the structural gene for CKS.

3. CKS Structural Gene

The sequence for the structural gene encoding CKS (the kdsB gene) is published in Goldman et al., J. Biol. Chem. 261:15831, 1986. The amino acid sequence for CKS derived from the DNA sequence is described in the same article.

Figure 3:
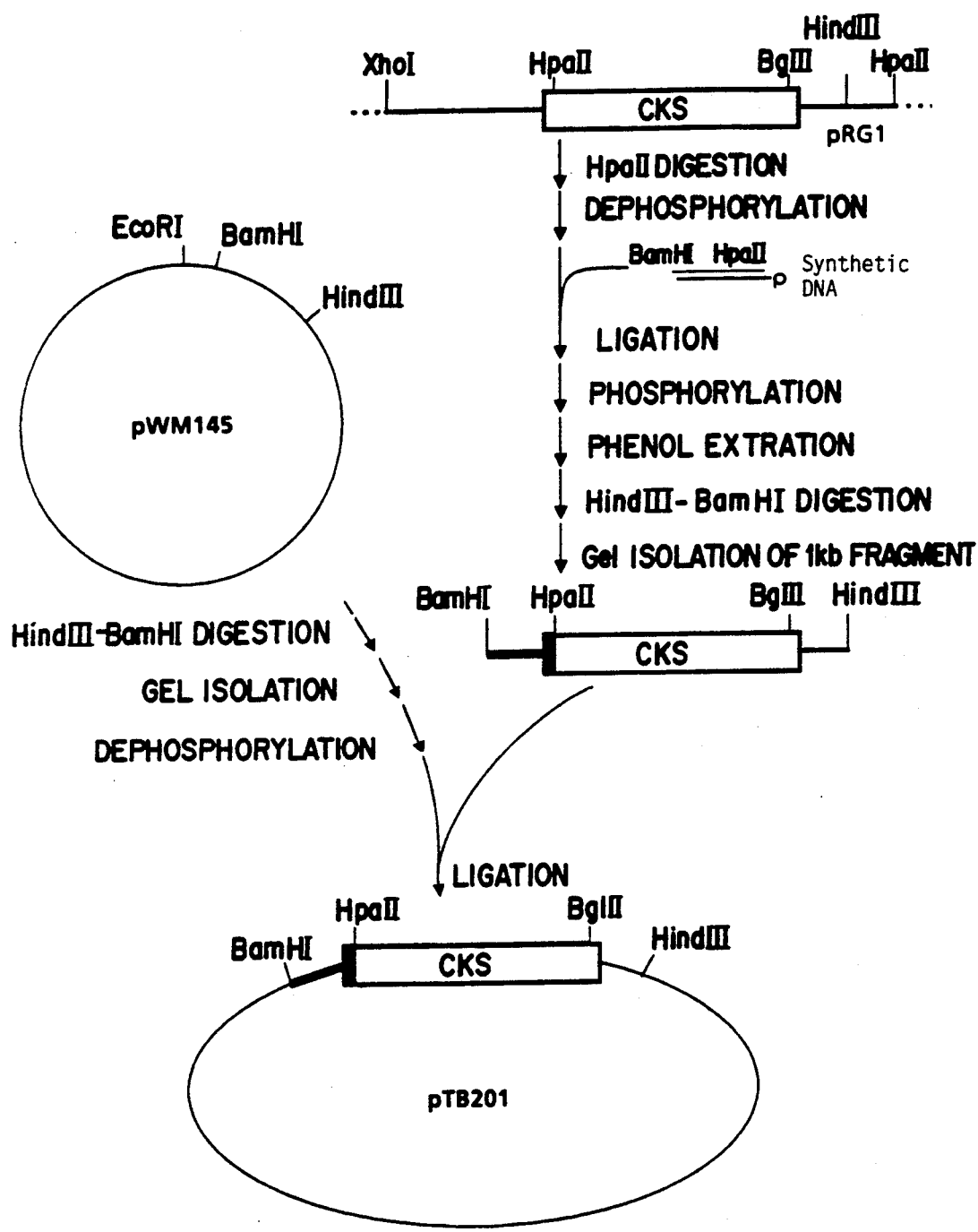
FIG. 3 is a schematic representation of the construction of pTB201 from pWM145.

The kdsB gene was obtained from Goldman's plasmid pRG1 (J. Bacteriol. 163:256) (FIG. 3). The first step in the kdsB gene isolation was a HpaII digestion of pRG1. Digestion with HpaII cleaved 51 base pairs from the 5' end of the gene.

A DNA fragment including the base pairs from the BamHI site to the HpaII site of FIG. 4 was constructed by annealing synthetic oligonucleotides (Example 1). This DNA sequence included the ribosome binding site as well as the 51 base pairs for the 5' end of the kdsB gene. The BamHI-HpaII fragment was then ligated to the HpaII native kdsB gene containing fragment, as described in detail in Example 1. As can be seen, the ligation replaced the 51 base pairs lost to kdsB, and added the ribosome binding site for the control region.

4. Construction of CKS Expression Vector

Figure 2:
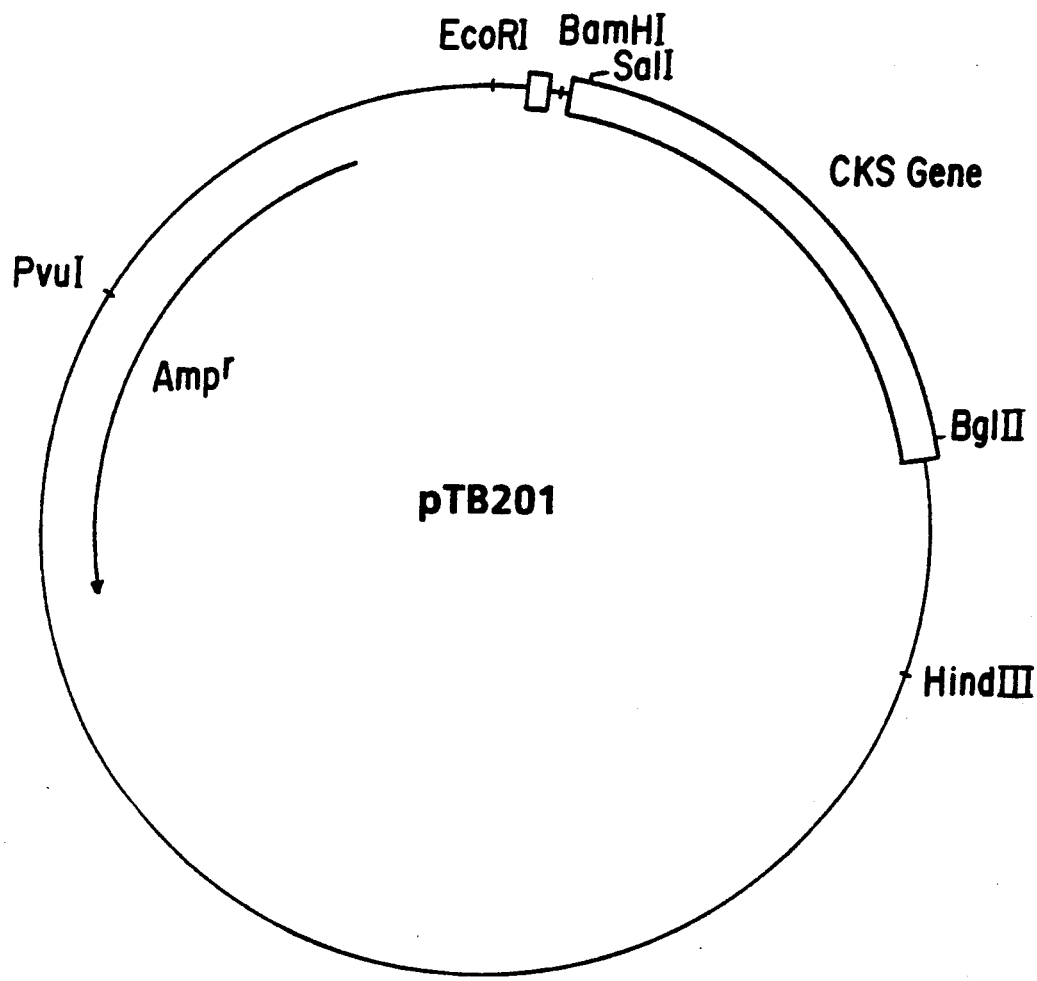
FIG. 2 is a graphic representation of a plasmid pTB201 containing a gene for CKS.

The pWM145 plasmid containing the modified lac promoter located between the EcoRI and BamHI sites shown in FIG. 4A was digested with BamHI and HindIII to provide an insertion site for the BamHI-HindIII fragment containing the CKS structure gene. (FIG. 3 The kdsB containing fragment was then ligated into the pWM145 vector, assembling the control region containing the modified lac promoter and the ribosome binding site in the process. This produced plasmid pTB201 (FIGS. 2 and 3).

Figure 7:
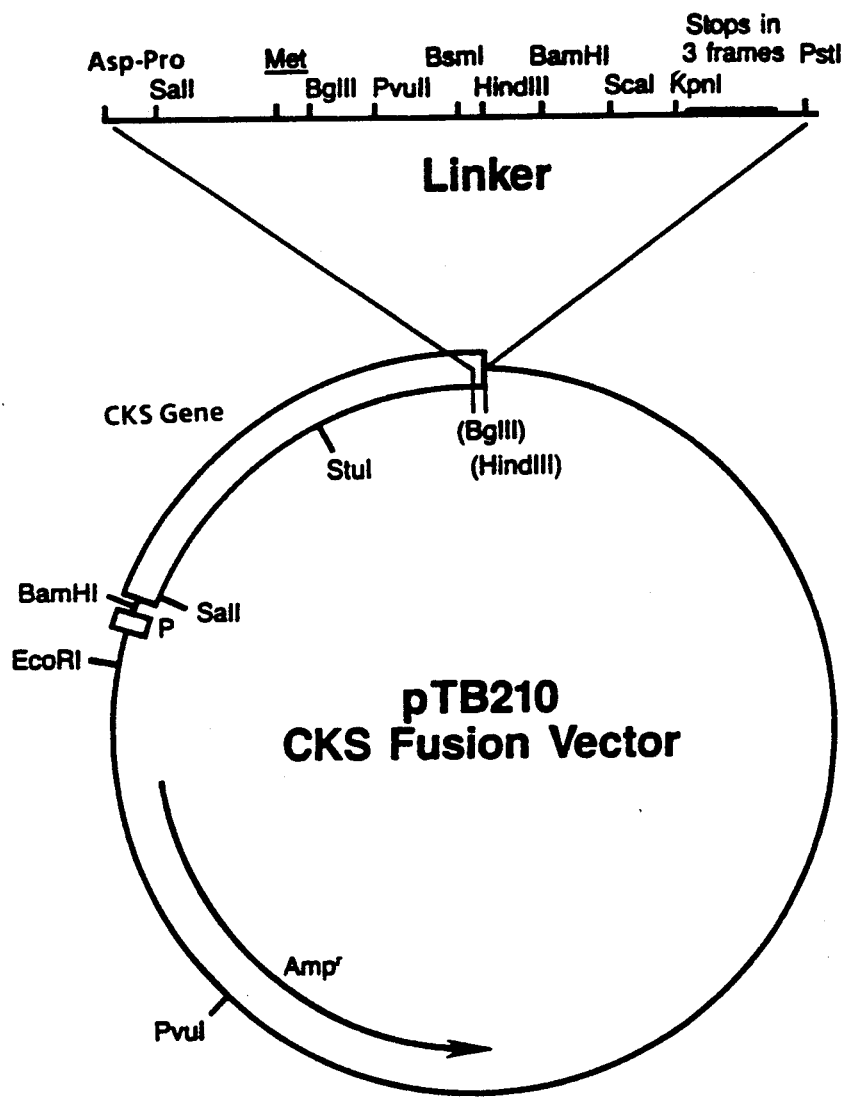
FIG. 7 is a graphic representation of a plasmid, pTB210, used to express HIV p41 fusion proteins.

5. Insertion of Linker Allowing Cloning of Heterologous Genes pTB201 is a fusion expression vector for heterologous genes which have the appropriate reading frame when cloned into the BglII or the BglII-HindIII sites (FIG. 2). However, the versatility of pTB201 can be improved by introducing other restriction endonuclease cloning sites. This is shown in FIG. 7 where a linker containing multiple restriction sites replaces the BglII-HindIII fragment of pTB201 to produce a new vector, pTB210. The linker also includes a sequence coding for Asp-Pro which allows for cleavage of the CKS protein from the heterologous protein fused to it.

The linker of FIG. 7 also includes stop codons in all three reading frames, placed downstream of the restriction sites. Thus, no matter what heterologous structural gene or portion thereof is inserted in the linker, translation will terminate immediately after the inserted gene.

6. Insertion of Heterologous Genes into pTB210

Insertion of heterologous genes into a plasmid of this invention can be accomplished with various techniques, including the techniques disclosed in European Patent Publication Number 253,193 entitled "Method for Mutagenesis By Oligonucleotide-Directed Repair of a Strand Break" and in Japanese Patent Application Number 002348/1990, laid open to public inspection Jan. 8, 1990, entitled "Method for Mutagenesis by Oligonucleotide-Directed Repair of a Strand Break" which are incorporated herein by reference.

7. Examples

The Examples below illustrate the concepts explained above. Example 1 described the construction of a plasmid pTB201 which contains a modified lac promoter and the kdsB gene. In Example 2, cells containing pTB201 are used to express the CKS protein to establish that the kdsB gene is functional. In Example 3, goat anti-CKS sera is raised to detect the fusion proteins such as the one produced in Example 4. In Example 4, a fusion protein of CKS and HIVI p41 is disclosed. In Example 5, fusion proteins of CKS and various permutations of synthetic HIVI p41 and p120 are disclosed. In example 6, a fusion protein of CKS and HSVII gG2 is disclosed. In Example 7, a fusion protein of CKS and the "kringle" region of tPA (tissue-plasminogen-activator) is prepared. In Example 8, two fusion proteins of CKS and SPL(pVal) are prepared. In Example 9, a fusion for CKS and SPL(phe) is prepared. In Example 10, a fusion for CKS and HIV-2 is prepared.

EXAMPLE 1

CKS Expression Vector

A. Construction and Preparation of pWM145

The plasmid, pWM145, is a derivative of the C5a expression vector, pWM111. (mandecki et al, Gene 43:131, 1986) Whereas the pWM111 vector contains a lacP-UV5-D24 promoter, the pWM145 vector contains a lacP-T9-D23 promoter. The changes were accomplished by replacing the promoter/operator region of pWM111 contained within an EcoRI-BamHI fragment with asynthetic fragment (FIG. 4A) containing the modifications. The following procedure was used.

Plasmid DNA (pWM111) was isolated from JM83 (ara, (lac-proAB), rpsL, o80, lacZ M15) cells using a standard alkaline extraction protocol followed by purification on a cesium chloride gradient and precipitated with three volumes of 70% ethanol at −20° C. for two hours followed by centrifugation. DNA was resuspended in distilled water to a concentration of 1 mg/ml.

One microgram of pWM111 DNA was digested for two hours concomitantly with ten units of EcoRI and ten units of BamHI in 20 ul of a buffer consisting of 50 mM Tris, pH7.5; 10 mM $MgCl_2$; and 100 mM NaCl. Following digestion, the three kilobase plasmid was purified by 5% (50:1 acrylamide:BIS) polyacrylamide gel electrophoresis (PAGE). The fragment was cut out and extracted by shaking overnight at 37° C. in 10 volumes of 500 mM ammonium acetate, 10 mM magnesium acetate, 1 mM EDTA, and 0.1% SDS. The DNA was precipitated by chilling it for two hours at −20° C. with 2.5 volumes of 100% ethanol, followed by centrifugation.

The EcoRI-BamHI promoter fragment was composed of four oligonucleotides (oligos 1 through 4 indicated by brackets in FIG. 4A) which were purified by 20% PAGE under denaturing conditions and annealed by mixing equal molar amount of the oligonucleotides together in ligation buffer (66 mM Tris, pH7.6; 6.6 mM $MgCl_2$; 50 ug/ml BSA; 10 mM dithiothreitol; 1 mM ATP), maintaining the mixture at 80° C. for five minutes, cooling the mixture slowly to 25° C., then refrigerating for one hour. A ten fold molar excess of annealedoligonucleotides was ligated together with approximately 50 ng of the purified EcoRI-BamHI digested vector and one unit T4 ligase in 20 ul volume ligase buffer at 16° C. overnight. One-fourth of the ligation mix was used to transform competent JM103 (supE, thi, (lac-proAB), endA, rpsL, sbcB15, [F', traD36, proAB, lacI$^q$ Z M15) using standard protocol (Mandel & Higa, J. Mol. Biol. 53:154,1970). Plasmid DNA from the transformants was prepared from 150 ml cultures as described above, and the DNA was sequenced using Sanger methodology (Proc. Natl. Acad. Sci. USA 24:5463,1977).

B. Construction and Preparation of pTB201

The kdsB gene from *E. coli* K-12, which encodes CTP:CMP-3-deoxy-D-manno octulosonate cytidylyltransferase (CMP-DKO synthetase), was isolated from pRG1. The gene is almost entirely contained within a HpaII fragment (FIG. 3). A linker was constructed to facilitate cloning kdsB into pWM145. The linker not only provided a BamHI site for subsequent cloning but also included a strong ribosome binding site, and the DNA sequence coding for 17 amino acids at the amino terminus of CKS (FIG. 4B). The procedure for construction, shown in FIG. 3, was as follows:

1a. Plasmid pRG1 was digested with HpaII and dephosphorylated with bacterial alkaline phosphatase (BRL). The 1.7 kb kdsB gene fragment was isolated on a 5% (50:1) Acrylamide:BIS gel, eluted, and purified as described above.

1b. Oligonucleotides (shown in FIG. 4B) were synthesized, purified, labeled (using BRL T4 Kinase, with a 2X molar excess of ATP [1 part gamma [$^{32}$P]ATP to 9 parts nonradioactive ATP] and BRL recommended protocol) and annealed.

2. Ligation of the HpaII gene fragment with the synthetic fragment was carried out at 16° C. overnight. Ligase was heat inactivated (15 min at 65° C.) DNA was then phosphorylated (as above), phenol extracted (1X 1 vol buffer equilibrated phenol, 1X 1 vol chloroform:isoamyl alcohol), ethanol precipitated, and resuspended in medium salt buffer (50 mM Tris, pH 7.5, 10 nMM, $Cl_2$, and 50 mM NaCl). Following simultaneous digestion with HindIII and BamHI, the DNA was purified from a 5% (50:1) acrylamide gel.

3. The pWM145 vector was digested with HindIII and BamHI, dephosphorylated, and purified from a 5% (50:1) acrylamide gel as above. The vector (15 ng) and insert (20 ng) were ligated overnight at 16° C. One half of the total ligation mix was used to transform competent JM103 cells. The pTB201 construct was verified by DNA sequencing.

EXAMPLE 2

Expression of kdsB Gene and Purification of CKS From pTB201/JM103 Cells

A. Cultivation of pTB201/JM103 cells

Figure 5:
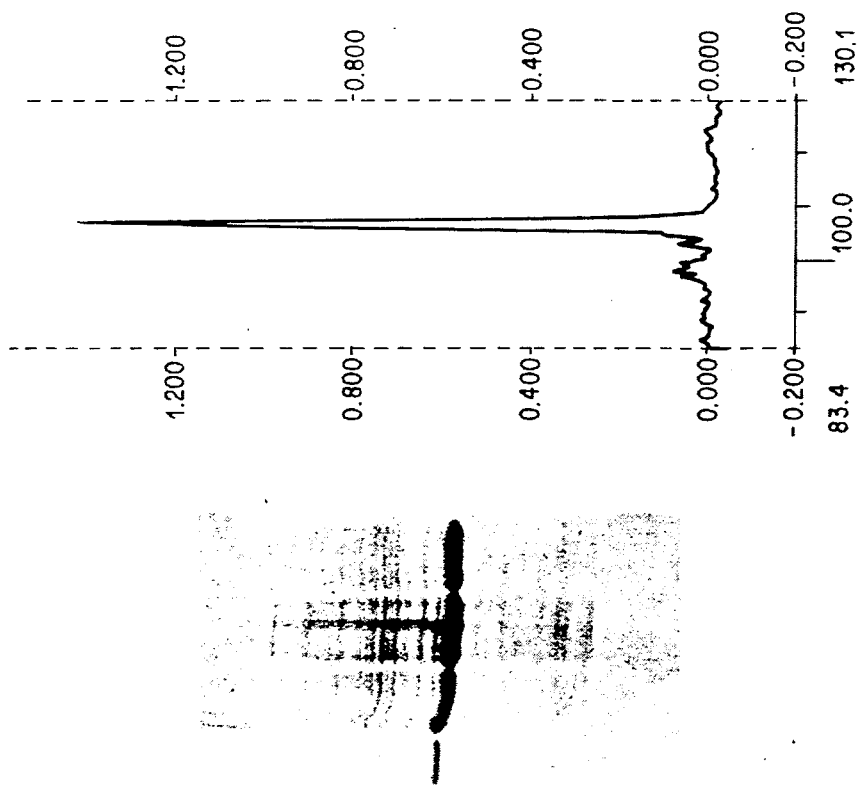
FIG. 5 is a coomassie brilliant blue-stained gel of various amounts of whose cell lysate from pTB201-containing JM103 cells. A corresponding gel scan/integration is also shown.

A 50 ml flask containing 10 ml LB broth with 50 ug/ml ampicillin was inoculated with a loopful of frozen stock pTB201/JM103 cells. The culture was incubated at 37° C. while shaking at 225 RPM. When the culture become turbid, the 10 ml were used to inoculate one liter of LB/Amp in a four liter flask. At an $OD_{600}=0.3$, IPTG (isopropyl-thio-$\beta$-galactoside) was added to a final concentration of 1 mM, and the cells were incubated overnight. A typical SDS-PAGE of the whole cell lysate as well as a gel scan on the sample is shown in FIG. 5. The relative percentage of the CKSto the total cellular proteins is 50 to 75%.

B. Purification of CKS

Purification procedure was that described by Goldman and Kohlbrenner (J. Bacteriol. 163; 256–261) with some modifications. Cells were pelleted by centrifugation, resuspended in 50 mM potassium phosphate (pH 7.6), and lysed by two passages through a French Press (15,000 PSI). The lysate was spun at 30,000 X g for 30 minutes. The soluble fraction was treated with protamine sulfate and ammonium sulfate, and dialyzed as described (Ray et al, Methods Enzymol. 83:535 1982). The sample was passed for final purification through a BioRad DEAE-5 PW HPLC-ion exchange column and eluted with a 50–400 mM potassium phosphate (10% acetylnitrile) gradient.

EXAMPLE 3

Generation of Goat Anti-CKS Sera

A. Goat immunization and bleeding

A goat was immunized monthly in three general areas—inguinal (subcutaneously), auxillary (subcutaneously) and hind leg muscles. Initial inoculation consisted of 1 mg purified CKS in complete Freund'Adjuvant. Thereafter, the boosting inoculum consisted of 0.5 mg purified CKS in incomplete Freund's Adjuvant. Five-hundred milliliters of blood was collected from the goat two and three weeks post-inoculation starting after the second boost. The blood was allowed to clot overnight, and the serum was decanted and spun at 2500 RPM for thirty minutes to remove residual red blood cells.

B. Immunoblotting

Figure 6:
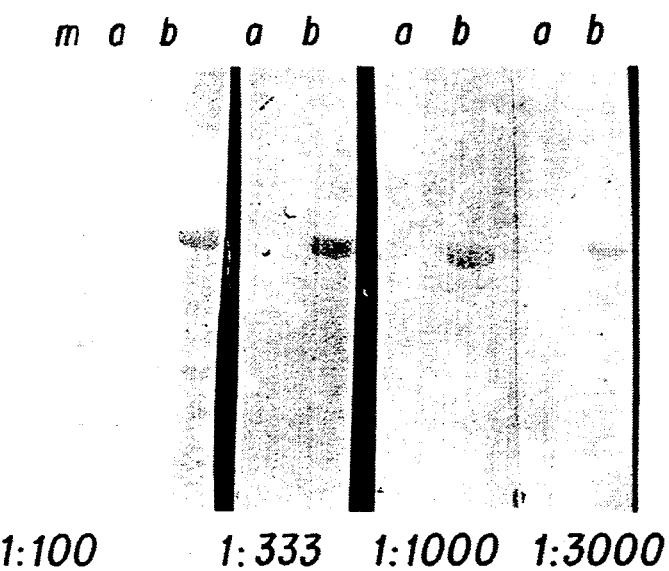
FIG. 6 shows immunoblots of CKS-producing and nonproducing cells used to optimize the titration of goat anti-CKS serum for identifying CKS fusion proteins. M is protein molecular weight markers; A, negative control JM103 whole cell lysate; B, positive control pTB201/JM103 whole cell lysate.

The presence of anti-CKS antibodies in the goat serum was confirmed by immunoblotting (FIG. 6). Whole cell lysates of pTB201/JM103 (labeled "b" in FIG. 6) and JM103 (labeled "a") controls were run on a 12.5% SDS-polyacrylamide gel, and proteins were electrophoretically transferred (Towbin, et al, Proc. Natl. Acad. Sci. USA 76:4350) to nitrocellulose. The filter was cut into strips which were pre-blocked with immunoblot buffer (5% instant dry milt, 1 X TBS [50 mM Tris, pH 8.1; 150 mM NaCl], 0.01% Antifoam C Emulsion) for fifteen minutes with agitation. Strips were placed into separate containers with immunoblot buffer and various amounts of serum (from 1:100 to 1:3000) were added. After one and one-half hours of agitation, the buffer was poured off, and the strips were washed three times for five minutes with 1 X TBS. The second antibody, horseradish peroxidase-labeled rabbit anti-goat (BioRad), was added to the strips at a 1:1500 dilution in immunoblot buffer. Following one and one-half hours of agitation, the buffer was poured off, and the strips were washed as above. Blots were developed for 5-10 minutes with agitation after addition of the developing agent (0.5 mg/ml of 3,3'-diaminobenzidine tetrahydrochloride dihydrate, 0.1 ug/ml of $H_2O_2$ in 1 X TBS). A 1:3000 dilution of the serum was optimal, giving strong positive bands and negligible background.

EXAMPLE 4

Fusion protein—CKS/HIVI p41 HaeIII-HindIII

Figure 8:
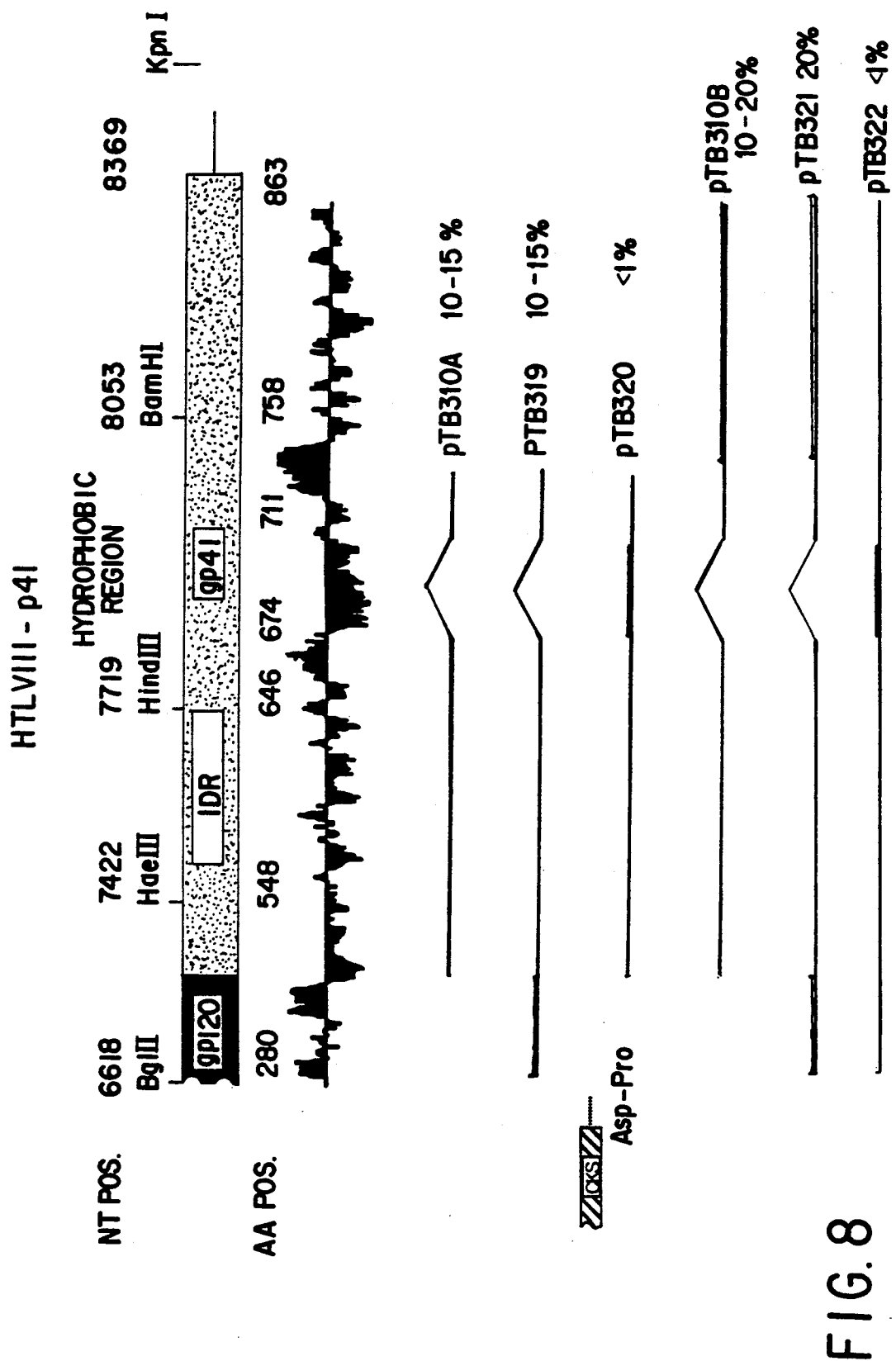
FIG. 8 shows a representation of the various synthetic p41 genes relative to the native gene. A hydrophobicity plot of the protein is also indicated. Levels of expression of each clone are included.

As an example of expression of a hybrid gene, a portion of the HIVI (human immunodeficiency virus I) p41 (envelope) gene was cloned into the CKS expression vector. The resulting gene coded for a protein fusion which consisted of CKS (less nine residues at the carboxy terminus), a nine amino acid residue linker, and a major epitope of the HIVI virus (amino acid positions 548-646 based on the precursor envelope protein, p160, numbering by Ratner, et al. Nature 313:227, 1985) (refer to FIG. 8). In order to assure the proper reading frame of the HIVI portion of the gene, a linker was designed and cloned into the pTB201 plasmid. The linker and HIVI gene fragments were cloned as close to the distal end of the kdsB gene as conveniently possible. Our rationale was that maximizing the amount of kdsB gene would maximize the change of success for high level expression of the heterologous gene.

A. Construction of pTB210

The pTB210 plasmid, American Type Culture Collection Deposit Number ATCC 68297, deposited Apr. 10, 1990 (FIG. 7) was a derivative of the pTB201 plasmid (described above). pTB201 was digested with BglII and HindIII, and the 3.6 kb vector fragment was purified from a 5% (50:1) acrylamide gel. The linker, composed of two synthetic oligonucleotides with overhands compatible with BglII and HindIII ends, was ligated into the vector, and the ligation mixture was used to transform competent JM109 cells (recA1, endA96, thi, hsdR17, supE44, relA1, λ-, (lac-proAB), [F', traD36, proAB, lac I$^1$Z M15]). DNA sequencing was used to confirm the construction.

B. Construction of pTB211

The pTB211 plasmid was the vector construction used to express the hybrid kdsB-HIVI p41 major epitope gene. The source of HIVI DNA was a plasmid which contained the p160 gene of HIVI (HTLVIIIB isolate from NIH) cloned as a KpnI fragment into pUC18. The plasmid was digested with HaeIII and HindIII and a 296 bp fragment was isolated from a 5% acrylamide gel. This fragment was ligated into PvuII-HindIII digested pTB210 vector followed by transformation into competent JM109 cells.

C. Screening of Transformants

The transformed cells were plated on LB/AMP plates. Following overnight incubation at 37° C., several colonies were picked from the plate and used to inoculate 2 ml of LB/Amp broth. Cultures were grown to an $OD_{600}$ of 0.3-0.5 then IPTG was added to a final concentration of 1 mM. Cultures were shaken at 37° C. for an additional three hours. The absorbance of the cultures at 600 nm was measured; cells from one milliliter of each culture were precipitated by centrifugation, and then resuspended to an $OD_{600}$ equivalent of ten in treatment buffer (63 mM Tris, pH 6.8, 2%SDS, 10% glycerol, 5% 2-mercaptoethanol). Following a 10 minute incubation in a boiling waterbath, an aliquot (10 ul) of each lysed culture was elecrophoresed on 12.5% SDS-polyacrylamide gels. A protein band corresponding to the proper molecular weight of the fusion protein could be visualized directly on gells stained with Commassie brilliant blue. Fusion protein could also be detected by immunoblots using the goat anti-CKS serum (method described in Example 3B.) and HIVI positive human serum (using human serum at 1:250 dilution and HRP conjugated goat anti-human antibodies at 1:1500). The fusion protein level in the cells after induction was 5-10% of the total cellular protein.

EXAMPLE 5

Fusion protein—CKS/synthetic HIVI envelope peptides

In this example, hybrids of the kdsB and portions of a synthetic p41 genes expressed and produced fusion proteins to a level of up to 20% of the total cellular protein. Additionally, this example demonstrates the use of an Asp-Pro dipeptide in the linker region as a chemical cleavage site for cleaving the CKS portion of the protein from the HIVI portion. Further examples are included which demonstrate that multiple fusions (CKS peptide plus p41 and a portion of pl20) were attainable. These are useful peptides for diagnostics.

A. Synthesis and cloning of the HIVI synp41d gene

The synp41d gene codes for a deletion mutant of the HIVI p41 protein which contains a 38aa hydrophobic region deletion (from Ala674 to Bal711 based on p160 numbering, refer to FIG. 8 plasmid, pTB310B). The gene was synthesized using the method of oligonucleotide directed double-standard break repair disclosed in European Patent Publication Number 253,193 and Japanese Patent Application Number 002348/1990, laid open to public inspection Jan. 8, 1990 which are incorporated herein by reference. The specific sequence is indicated by single-line overscore on FIG. 9. The synthetic gene contained flanking BamHI and KpnI sites to facilitate cloning into pTB210. The vector was digested with BglII and KpnI, and the BamHI-KpnI synthetic gene fragment was ligated into the vector. Following transformation into JM109 cells, clones were cultivated, induced, and screened for expression.

B. Characterization of fusion protein encoded by pTB301A

Upon the initial screening, a clone was discovered containing a plasmid (pTB310A) which had a A/T base deletion at nucleotide position 813 (based on FIG. 9 numbering) Although this mutation (which occurred in cloning the synthetic p41d gene) resulted in a truncation in the p41d portion of the fusion protein, the protein produced was characterized for its diagnostic potential.

PRODUCTION AND PURIFICATION

Ten ml of LB/Amp in a 100 ml flask was inoculated with 100 ul of an overnight pTB310A/JM109 culture. After shaking at 37° C. for one and one-half hours, IPTG was added to the culture to a concentration of 1 mM, and the cells were grown for four more hours. An aliquot (1 ml) of the culture was pelleted and lysed in a an appropriate volume of 1 X treatment buffer to give a final concentration of cells of 10 $OD_{600}$ absorbance units. This sample, referred to as WCL (whole cell lysate), was used to measure the amount of fusion protein relative to total cellular proteins. The remaining 9 ml of cell culture was centrifuged (five minutes, 5000 rpm) and the cells were resuspended in 10 mM Tris (400 ul), pH8.0, 1 mM EDTA with 2 mg/ml lysozyme. After fifteen minutes on ice, 10 ul of 20% Triton X-100 was added, and the cells were sonicated (6 X 30 sec). The lysate was spun in an Eppendorf centrifuge for five minutes. The supernatant was collected, and the pellet was resuspended in 8M urea (400 ul). The fusion protein present in the resuspended pellet fraction is about 75% pure based on Commassie stained gels.

WESTERN AND IMMUNOBLOTS

Figure 10:
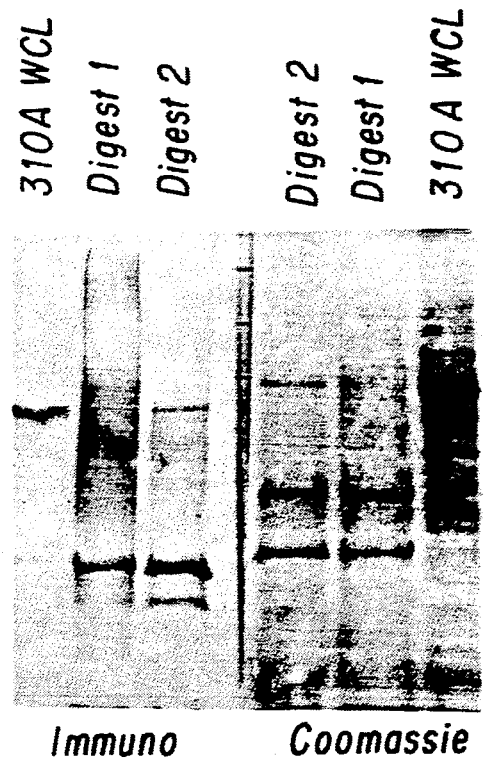
FIG. 10 illustrates the acid hydrolysate of the fusion protein expressed from pTB310. Coomassie brilliant blue-stained SDS-PAGE is pictured on the right. An immunoblot of an SDS-PAGE using human AIDS positive serum is shown on the left. Refer to text, Example 5B, for details.

A sample (10 ul) of pTB310A/JM109 WCL was loaded on a 0.7 mm thick 12.5% SDS-polyacrylamide gel, along with prestained protein molecular weight standards, WCL from JM109 without plasmid, and WCL from JM109 containing pTB210 (unfused CKS). Gel was run at 150 volts and terminated when bromophenol blue sample loading dye had reached the bottom of the gel. Proteins were then electrophoretically transferred to nitrocellulose. Immunoblotting was carried out as described in Example 3B. AN example of pTB310A/JM109 WCL on a standard gel and immunoblot is shown in FIG. 10.

CHEMICAL CLEAVAGE OF FUSION PROTEIN

An aliquot (30 ul) of the urea soluble fraction was diluted with ten volumes of water, and the insoluble fusion protein was pelleted by centrifugation. The protein was then dissolved in 30 ul of 6M guanidine hydrochloride, and 70 ul 98% formic acid added (Digestion 1). In a parallel experiment, 70 ul 98% formic acid was added to an aliquot (30 ul) of the urea fraction directly (Digestion 2). Following two days incubation at 42° C., ten volumes of water were added, and the insoluble proteins were pelleted by centrifugation. The pellet was resuspended in 1X treatment buffer (100 ul), and 10 ul was used per well on 12.5% SDS-polyacrylamide gel. FIG. 10 shows a sample of the cleaved products (Digestion 1 and Digestion 2) both on a Commassie-stained gel and an immunoblot (using HIVI positive human serum as primary antibody). Only two major bands are visible on the Commassie-stained gel. These represent the products of cleavage at the unique Asp-Pro bond: the CKS portion, MW=26.5 kDa and the p41 portion, MW=23.5 kDa. Peptide sequencing confirmed that the lower molecular weight band was indeed the p41 peptide, and that the amino terminal residue was proline which results from expected cleavage between the Asp and Pro.

C. Characterization of the pTB310B/JM109 clone

The clone containing the correct gene for the CKS-p41d fusion, pT310B, was cultured and assayed for expression. The fusion protein represents 10–20% of the total cellular protein (dependent on growth and induction conditions).

D. Addition of the p120 carboxy terminal region

A synthetic DNA fragment which encoded the carboxy terminal 42 amino acids of HIVI p120 (Insert 1, FIG. 9) was inserted into the NarI site of pTB310A and pTB310B at nt 15. The resulting clones pTB319/JM109 and pTB321/JM109, respectively, expressed the triple fusion protein at levels of up to 20% total cellular protein.

EXAMPLE 6

Fusion protein—CKS/HSVII gG2

A 1.1 kb fragment containing the Herpes Simplex Virus II (HSVII) gG2 gene (encoding a major envelope glycoprotein) was isolated following digestion with AatII and XbaI. A synthetic linker was ligated to the XbaI end to generate an AatII end. Both ends were then made blunt by treating the 3' overhangs with T4 polymerase.

Figure 11:
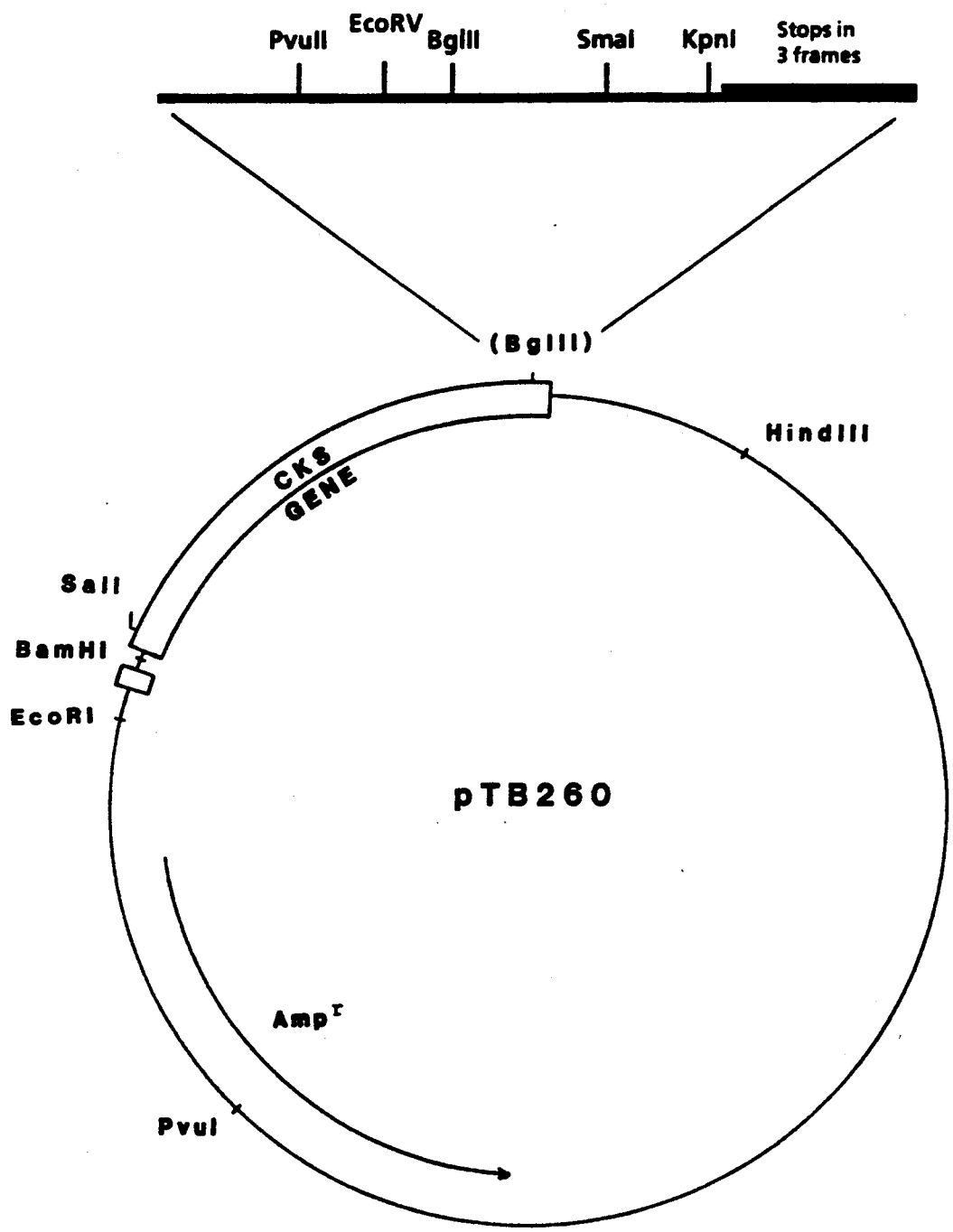
FIG. 11 is a graphic representation of a plasmid pTB260 used as a cloning vehicle in this invention.

The vector in this example was pTB260 (FIG. 11). It was constructed by ligating a synthetic fragment with multiple restriction sites into the BglII site of pTB201. In cloning the fragment, the original BglII site from pTB201 was inactived and thus, the BglII site in the linker 8 fragment is unique.

To facilitate cloning the blunt-ended DNA fragment containing the gG2 gene and to put the gene in the proper reading frame of kdsB, the BglII digested pTB260 was made blunt-ended by filling in the overhangs using Lenow and dNTP's. Following ligation of the gG2 DNA with pTB260, the DNA was used to transform competent TB-1 cells. Whole cells lysate from transformants run on gels and immunoblotted with rabbit serum against HSVII proteins gave a visible band of the proper molecular weight.

EXAMPLE 7

Fusion protein—CKS/Kringle region of tPA

Figure 12:
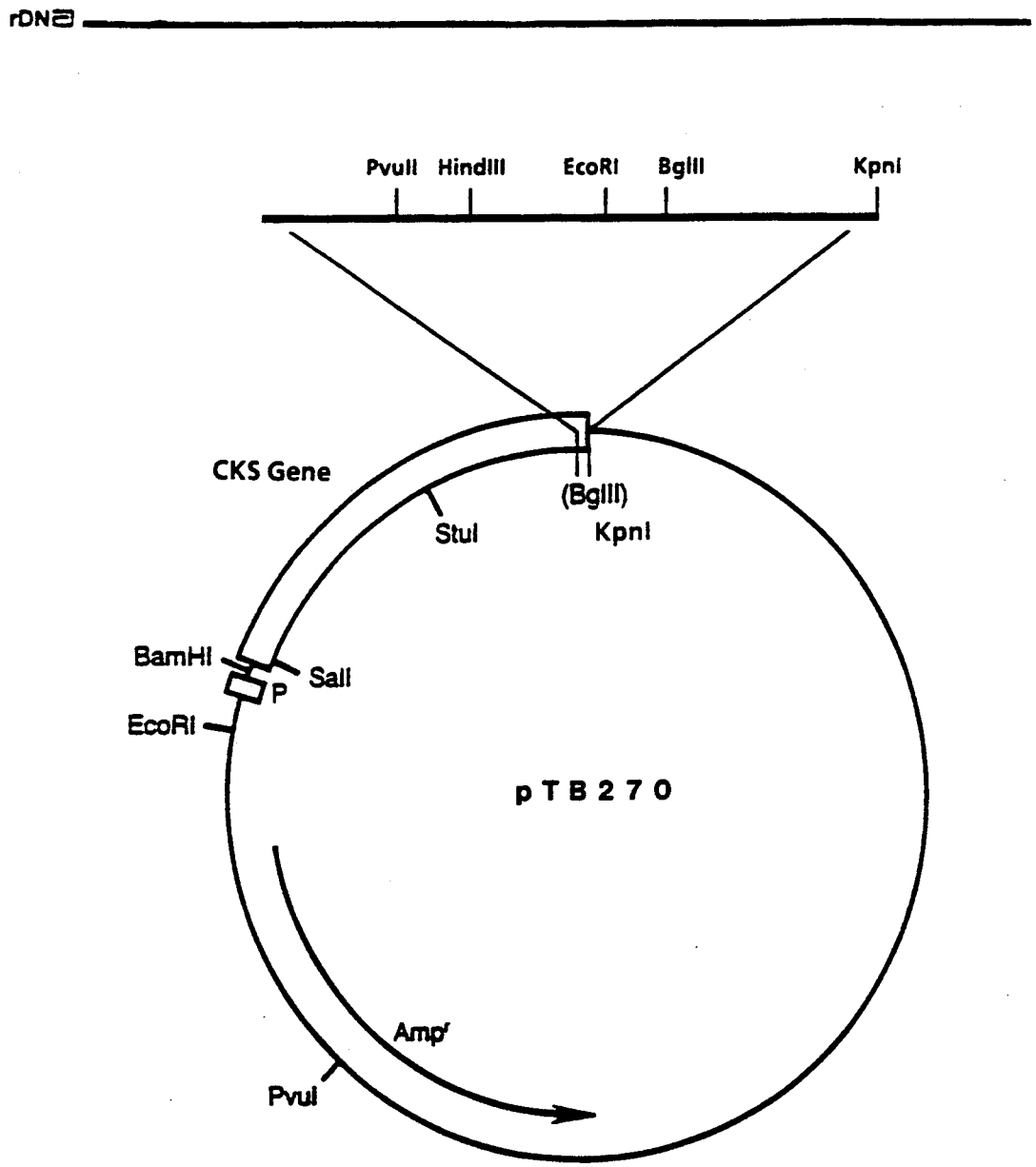
FIG. 12 is a graphic representation of a plasmid pTB270 used as a cloning vehicle in this invention.

A gene coding for the "kringle" (Patthy, L., *Cell*, 41:657 (1985)) region of tissue-plasminogen-activator was synthesized and cloned as a 335 bp HindIII-KpnI fragment into pTB270 (Zablen, L. B., unpublished). The pTB270 vector (FIG. 12) was a derivation of pTB210 which was constructed by ligating a synthetic multi-cloning site linker into BglII-KpnI digested pTB210. The pTB270 plasmid was then digested with HindIII-KpnI and ligated with the Kringle-region gene fragment. Transformation was carried in competent XL-1 Blue cells (stratagene). Clones containing the proper insert were confirmed by DNA sequencing of the plasmids. The level of the fusion protein reached 30%–40% of the total cellular proteins.

The CKS/Kringle protein was extracted from a culture by lysing the cells as in Example 5B, precipitating the cellular debris, and collecting the supernatant which contained the soluble fusion protein. Further purification was accomplished by "salting out" the protein. Briefly, ammonium sulfate was added to 10% (w/v), and the insuluble proteins were pelleted by centrifugation. The pellet of this fraction, after assaying to demonstrate the absence of fusion protein, was discarded. Ammonium sulfate was added to the supernatent to a final concentration of 30%, and the insoluble proteins were pelleted. This pellet contained 70% of the starting fusion protein amount and was 75% pure.

EXAMPLE 8

Fusion protein—CKD/SPL(pVal)

A. A human lung surfactant gene, SPL(pVal) (International Publication No. WO88/03170 filed by Whitsett et al.), contained within an 820 bp EcoRI fragment was cloned into pTB210. The overhanging EcoRI ends were filled using Klenow and dNTP's. The blunt-ended fragment was then ligated into PvuII digested pTB210. Following transformation into competent XL-1 Blue cells (Stratagene), DNA was isolated from a number of transformants and mapped with restriction endonucleases to identify clones with the insert in proper orientation. Expression level of the fusion protein based on whole cell lysates was 3%. The protein could be purified to about 50% purity by cell lysis and pelleting as described in Example 5B. The fusion protein was used to generate antibodies against the SPL peptide by immunizing rabbits with gel purified product.

Figure 13:
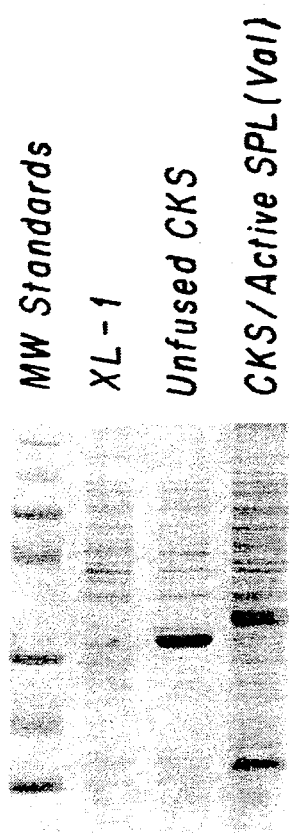
FIG. 13 is a coomassie brilliant blue-stained SDS-PAGE gel. Approximately equal numbers of cells of each clone type were lysed and loaded on the gel. The lane marked "XL-1" is the cell lysate from the XL-1 Blue strain with no plasmid. "Unfused CKS" is lysate from XL-1 Blue cells containing the pTB201 CKS-expressing vector. "CKS/Active SPL (Val)" is lysate from an XL-1 cell line which contains the active region of the pVal lung surfactant gene in fusion with the kdsB gene on the pTB201 plasmid.

B. A hybrid gene containing kdsB with the 139 nt active region of pVal was constructed by cloning a BglII-HindIII-ended synthetic fragment encoding the active region (refer to patent) into BglII-HindIII digested pTB201. Assays of whole cell lysates indicated that expression levels of up to 40% of the total cellular protein were obtained (FIG. 13).

EXAMPLE 9

Fusion protein—CKS/SPL(phe)

A human lung surfactant gene, SPL(phe) (disclosed in the Whitsett patent application above), contained within a 1635 bp EcoRI-HindIII fragment was cloned into pTB210. The gene was originally isolated from a clone, Phe 7-1, as a 1945 bp EcoRI fragment, blunt-end filled using Klenow and dNTP's, then digested with HindIII. This fragment was ligated into Pvu-HindIII digested pTB210 and transformed into competent XL-1 Blue cells. The CKS/SPL(phe) fusion protein level was 9% of the total cellular protein. The fusion protein was 50% pure in the pellet following lysis of the cells (procedure described in Example 5B). Gel purified CKS/SPL(Phe) was used to immunize rabbits to generate antibodies against the SPL(Phe) portion of the protein.

While several Examples of this invention have been provided, modifications to these Examples will be apparent to those of ordinary skill in the art. Such modifications are to be included in this invention, unless the claims which follow expressly state otherwise.

EXAMPLE 10

Fusion protein—CKS/synthetic HIV-2 TMP Fragment

In this example, a synthetic DNA fragment containing a portion of the HIV-2 (human immunodeficiency virus II) transmembrane protein (TMP) was cloned into the CKS expression vector. The resulting gene coded for a protein fusion consisting of CKS (less nine residues at the carboxy terminus), a ten amino acid residue linker, and the major epitope of the HIV-2 virus (envelope amino acid positions 502-609, numbering by Guyader, et al., *Nature* 326:662, 1987) followed by another ten amino acid residue linker. Thus fusion protein was expressed to a level of up to 15% of the total cellular protein and proved useful in the detection of sera containing HIV-2 antibodies.

A. Synthesis and cloning of the HIV-2 TMP fragment

Figure 15:
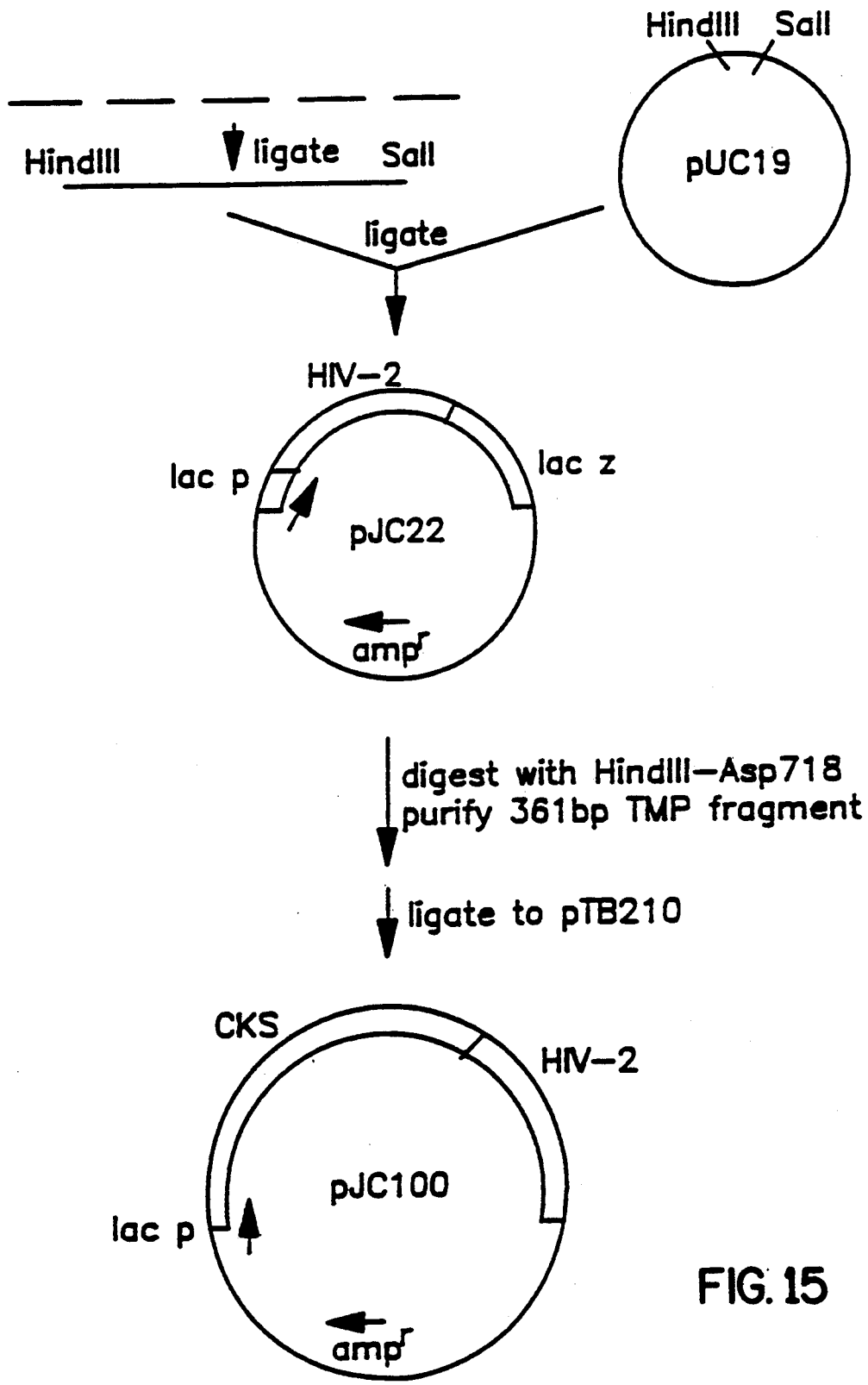
FIG. 15 is a schematic representation of the construction of pJC22 and pJC100.

The HIV-2 TMP fragment codes for the amino terminal 108 amino acids of the HIV-2 TMP (from Tyr 502 to Trp 609) identified in FIG. 14. The gene fragment was synthesized using the method of oligonucleotide directed double-stranded break repair disclosed in European Patent Publication No. 253,193 by Mandecki which is incorporated herein by reference. The five DNA fragments comprising the TMP gene fragment were ligated together and cloned at the HindIII-SalI sites of pUC19 (FIG. 15). A clone, designated pJC22, was identified by restriction mapping and its primary nucleotide sequence confirmed. The clone pJC22 was digested with HindIII-Asp718 to release a 361 bp fragment containing the synthetic HIV-2 TMP gene fragment which was ligated into the HindIII-Asp718 sites of plasmid pTB210 and transformed into XL1 cells. A clone, designated pJC100, was isolated and restriction mapped to identify the hybrid gene of kdsB and HIV-2 TMP.

B. Characterization of fusion protein encoded by pJC100

Figure 16:
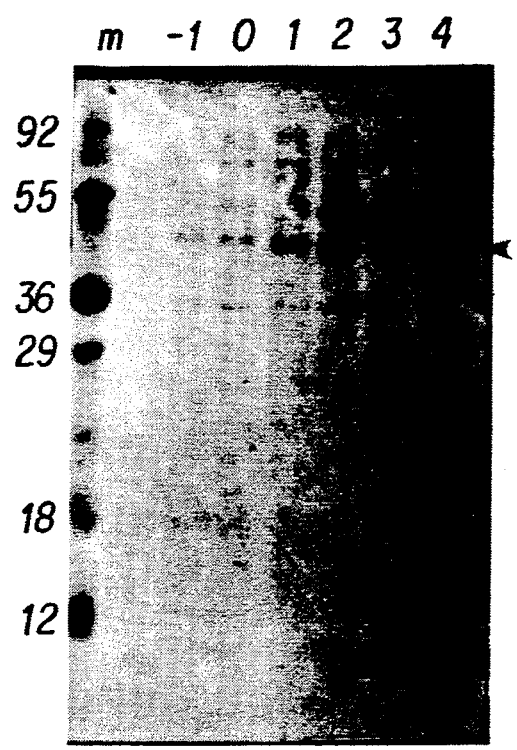
FIG. 16 is a coomassie brilliant blue stained gel of clone pJC100 induced for the specified time in hours. M is protein molecular weight markers.

Fifty-ml of LB/Amp in a 250 ml flask was innoculated with 500 l of an overnight culture of either pTB210/XL1 or pJC100/XL1 and allowed to shake at 37° C. until the $OD_{600}$ reached 0.5 absorbance units (1.5–2.0 hours) at which time IPTG was added to a final concentration of 1 mM. An aliquot (1.5 ml) of the culture was removed every hour for four hours and then a final aliquot taken at 18 hours post induction. These aliquots were pelleted and lysed in an appropriate volume of 1X treatment buffer to give a final concentration of cells of 10 $OD_{600}$ absorbance units. Aliquots of each timepoint (15 l) were electrophoresed on 12.5% SDS/PAGE gels and transferred electropohoretically to nitrocellulose. Immunoblotting was carried out as described in Example 3B using HIV-2 positive human sera or goat antibody directed against CKS. The HIV-2 positive human sera demonstrated no signal to the pTB210/XL1 culture and a strong signal to the pJC100/XL1 culture at the expected molecular weight. The goat antibody against CKS reacted strongly with both cultures at the expected molecular weights. A similar SDS/PAGE gel was run and Coomassie blue staining demonstrated that expression of the fusion protein peaked at 3–4 hours post induction at a level of 15% of total protein. FIG. 16 demonstrates the expression of the CKS/HIV-2 TMP fusion protein in a ten liter fermenter as seen by coomassie blue staining of a 12.5% SDS/PAGE gel of various time points before and after induction. A partial purification of the fusion protein was obtained by the method described in Example 5B with similar results.

We claim:

1. A method for expressing a protein in a prokaryotic cell, said method comprising the steps of:
   a) providing a DNA vector having:

1) a control region, said control region comprising a prokaryotic promoter and a prokaryotic ribosome binding site, wherein said control region directs expression of a DNA sequence comprising two elements operatively linked in a 5' to 3' direction, a first element encoding CKS protein; and 2) a second element encoding said protein to be expressed, wherein said two elements are contiguous and in the same reading frame;

b) transforming said prokaryotic cell with said DNA vector; and c) expressing a fusion protein of CKS protein and said protein to be expressed.

2. The method of claim 1 wherein said DNA vector includes an additional region located between said CKS region and said region encoding said protein to be expressed, wherein said additional region encodes a set of 1 to about 3 amino acids for site-specific chemical or enzymatic cleavage of said fusion protein.

3. The method of claim 1 wherein said prokaryotic promoter is a lacP-T9-D23 promoter comprising the sequence:

ATTAATGTGAGTTAGCTCACTCATTAGG-
CACCCCAGGCTTTACACTTTATG-
TTCCGGCTCGTATTTTGTGTGG.

4. The method of claim 1 wherein said protein is selected from the group consisting of human lung surfactant protein and proteins encoded by the viral genomes of HIV-1, HIV-2 and HSV-2 which are capable of reacting with appropriate antiserum.

5. The method of claim 4 wherein said protein is selected from the group consisting of proteins encoded by the viral genomes of HIV-1 or HIV-2 which are capable of reacting with appropriate antiserum.

6. The method of claim 1 wherein said DNA vector is provided by:
   a) providing plasmid DNA having a lacP-T9-D23 promoter;
   b) inserting a gene encoding CKS protein under the transcriptional-level control of said lacP-T9-D23 promoter; and
   c) inserting a DNA region encoding for said protein to be expressed at about the 3' end of said CKS gene wherein the final fusion product comprises said protein to be expressed and CKS protein.

7. A cloning vector for transforming cells to express heterologous protein, said cloning vector comprising a plasmid having a prokaryotic control region comprising a prokaryotic promoter and a prokaryotic ribosome binding site, wherein said control region directs expression of a DNA sequence comprising two elements operatively linked in a 5' to 3' direction, a first element encoding CKS protein and a second element encoding said protein to be expressed, wherein said two elements are contiguous and in the same reading frame.

8. The cloning vector of claim 7 wherein said promoter is a sequence substantially homologous to lacP-T9-D23 promoter comprising:

ATTAATGTGAGTTAGCTCACTCATTAGG-
CACCCCAGGCTTTACACTTTATG-
TTCCGGCTCGTATTTTGTGTGG.

9. A gene sequence for insertion into a plasmid vector, said gene sequence comprising in a 5' to 3' direction:
   a) a prokaryotic promoter;
   b) a prokaryotic ribosome binding site;
   c) a first gene fragment encoding CKS protein; and
   d) a second gene fragment encoding a protein to be expressed, wherein said first and second gene fragments are contiguous and in the same reading frame.

10. The gene sequence of claim 9 wherein said promoter is a synthetic promoter.

11. The gene sequence of claim 10 wherein said promoter is a lacP-T9-D23 promoter comprising the sequence:

ATTAATGTGAGTTAGCTCACTCATTAGG-
CACCCCAGGCTTTACACTTTATG-
TTCCGGCTCGTATTTTGTGTGG.

12. The gene sequence of claim 9 wherein said ribosome binding site if TAAGGAGGT.

13. The gene sequence of claim 9 wherein said first and second gene fragment are joined by a linker gene sequence which encodes for a protein sequence which is cleavable by a site specific chemical or enzymatic agent.

14. The gene sequence of claim 9 wherein said second gene fragment encodes a protein selected from the group consisting of human lung surfactant protein and proteins encoded by the viral genomes of HIV-1, HIV-2 and HSV-2 which are capable of reacting with appropriate antiserum.

15. The gene sequence of claim 9 wherein said second gene fragment is selected from the group consisting of gene sequences which encode for HIV-1, HIV-2 or HSV-2 proteins.

16. The gene sequence of claim 9 wherein said second gene fragment encodes for human lung surfactant.

17. The gene sequence of claim 9 wherein said second gene fragment encodes for bacterial proteins.

18. A plasmid vector comprising:
   a) a lacP-T9-D23 promoter;
   b) a ribosome binding site; and
   c) a gene sequence encoding CKS protein,
wherein said sequence encoding CKS protein is operatively linked to and under transcriptional control of said promoter.

19. The plasmid vector of claim 18 wherein said ribosome binding site is TAAGGAGGT.

20. The plasmid vector of claim 19 further including a transcription terminator.

21. The plasmid vector of claim 20 wherein said transcription terminator is a trpA rho independent terminator.

* * * * *